(12) United States Patent
Taylor et al.

(10) Patent No.: US 6,520,962 B1
(45) Date of Patent: Feb. 18, 2003

(54) TAPER-LOCKED ADJUSTABLE CONNECTOR

(75) Inventors: Harold Sparr Taylor, Memphis, TN (US); Matthew M. Morrison, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 206 days.

(21) Appl. No.: 09/694,702

(22) Filed: Oct. 23, 2000

(51) Int. Cl.[7] .............................................. A61B 17/56
(52) U.S. Cl. ............................ 606/61; 606/53; 606/54; 606/72
(58) Field of Search ........................... 606/53, 54, 61, 606/72, 73

(56) References Cited

U.S. PATENT DOCUMENTS

| | | | |
|---|---|---|---|
| 5,053,034 A | * 10/1991 | Olerud ......................... | 606/54 |
| 5,261,909 A | 11/1993 | Sutterlin et al. | |
| 5,474,551 A | 12/1995 | Finn et al. | |
| 5,591,166 A | 1/1997 | Bernhardt et al. ............ | 606/61 |
| 5,611,800 A | 3/1997 | Davis et al. | |
| 5,643,263 A | 7/1997 | Simonson .................... | 606/61 |
| 5,741,255 A | * 4/1998 | Krag et al. ................... | 606/61 |
| 5,776,135 A | * 7/1998 | Errico et al. ................. | 606/60 |
| 5,885,285 A | 3/1999 | Simonson .................... | 606/61 |
| 5,947,967 A | 9/1999 | Barker | |
| 5,976,135 A | * 11/1999 | Sherman et al. ............. | 606/61 |
| 6,050,997 A | 4/2000 | Mullane ....................... | 606/61 |
| 6,063,089 A | * 5/2000 | Errico et al. ................. | 606/60 |
| 6,086,588 A | 7/2000 | Ameil et al. ................. | 606/61 |
| 6,183,473 B1 | * 2/2001 | Ashman ....................... | 606/61 |
| 6,210,413 B1 | * 4/2001 | Justis et al. .................. | 606/60 |
| 6,231,575 B1 | * 5/2001 | Krag ............................ | 606/61 |

FOREIGN PATENT DOCUMENTS

EP    0 786 235 B1    4/2000    ........... A61B/17/58

* cited by examiner

Primary Examiner—Linda C. M. Dvorak
Assistant Examiner—Kenneth G Schopfer
(74) Attorney, Agent, or Firm—Woodard, Emhardt, Naughton, Moriarty & McNett

(57) ABSTRACT

A connection assembly between a spinal implant rod and a vertebral anchor. The assembly has a longitudinal member, a housing, a rod interface washer, and a compression member. The longitudinal member has an aperture at one end and a wedge at the other. The housing has a passageway to accept the shank of a bone screw and a bore to accept the wedge. The bore is open to the passageway so that when the wedge is pulled from the bore it pushes against the shank of the bone screw, trapping the bone screw between the wedge and the sidewalls of the passageway. Threading a setscrew into the aperture presses a spinal rod against the washer, presses the washer against the housing, and pulls the wedge against the shank of the bone screw. Further tightening of the setscrew then locks the bone screw and rod together.

25 Claims, 21 Drawing Sheets

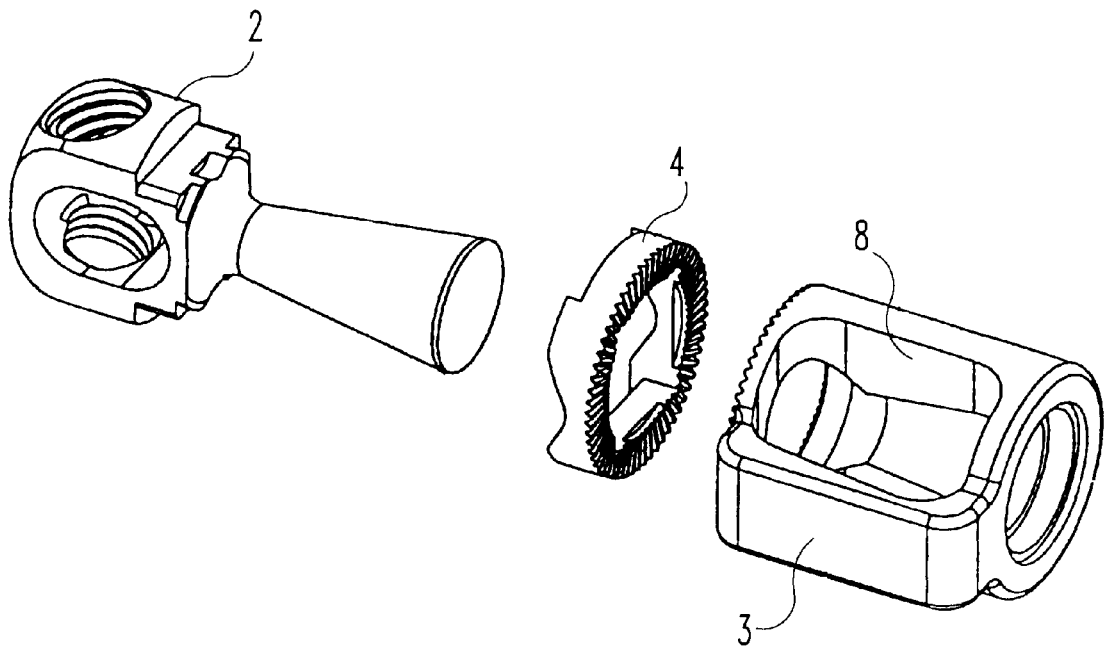
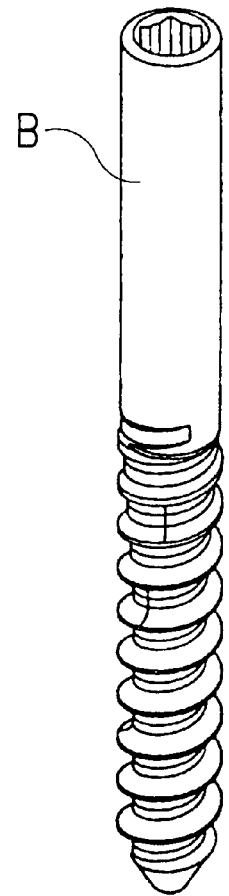
*Fig. 18*

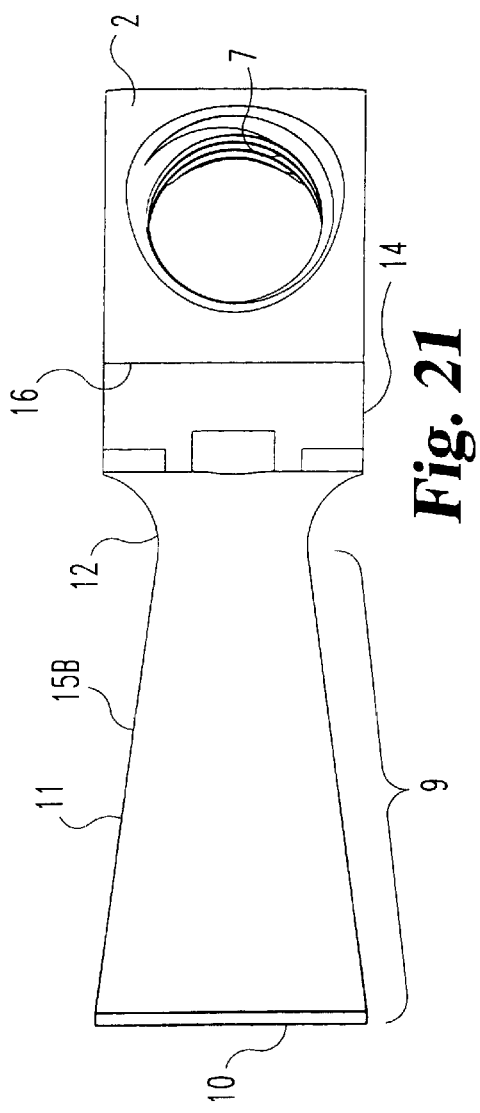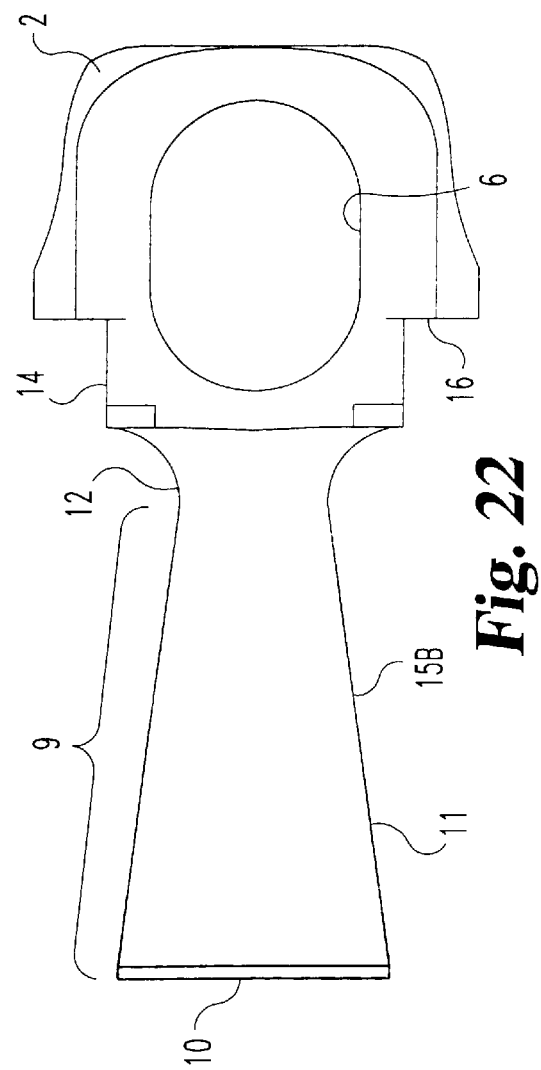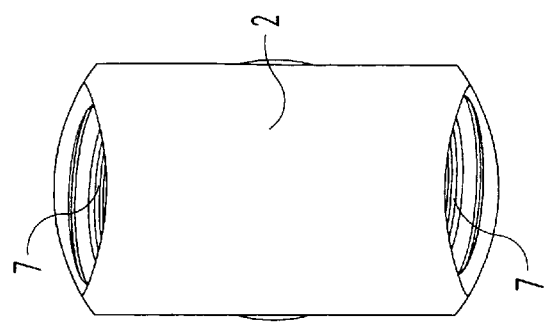

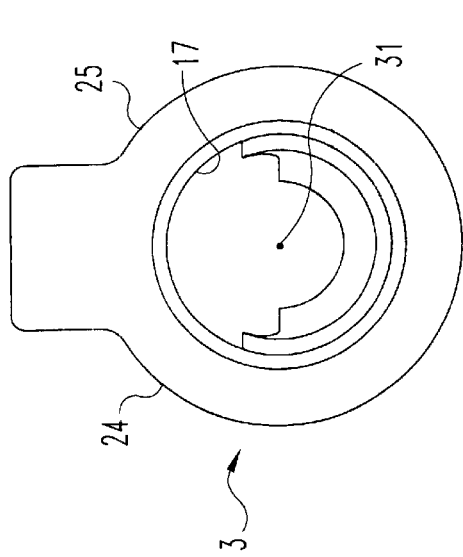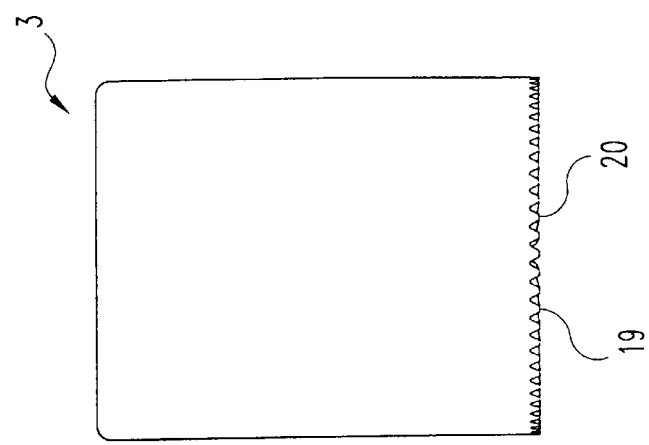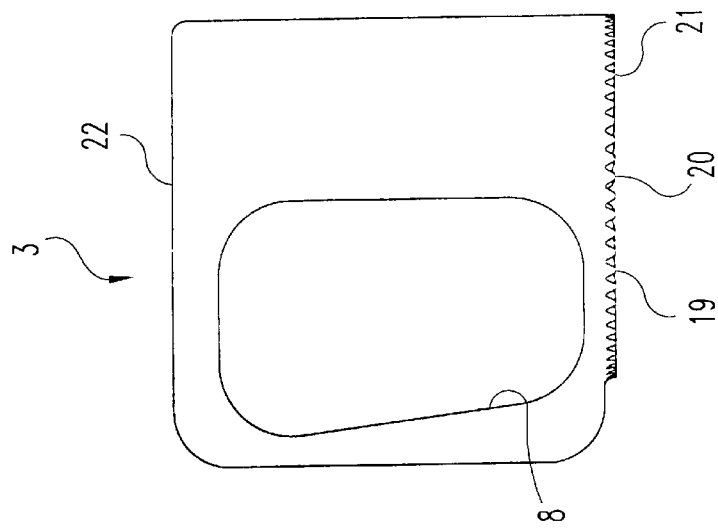

TAPER-LOCKED ADJUSTABLE CONNECTOR

This invention relates to a connection between a spinal rod and a vertebral anchor with a tapered locking surface that traps the vertebral anchor in the connection fitting.

BACKGROUND OF THE INVENTION

Spinal implant systems provide a rod for supporting the spine and for properly positioning components of the spine for various treatment purposes. Bolts, screws, and hooks are typically secured to the vertebrae for connection to the supporting rod. These vertebral anchors must frequently be positioned at various angles due the anatomical structure of the patient, the physiological problem being treated, and the preference of the physician. It is difficult to provide secure connections between the spinal support rod and these vertebral anchors at all the various angles and elevations that are required, especially where there are different distances between the rod and bolts and where these components are located at different heights on the patient.

What is needed is a connection assembly between a spinal rod and a vertebral anchor that allows the surgeon to fix the desired elevation between a rod and the bone anchor as well as fix the desired angle between the anchor and rod. The following invention is one solution to that need.

SUMMARY OF THE INVENTION

In one aspect, this invention is a connection assembly between a spinal implant rod and a vertebral anchor. The connection assembly includes a longitudinal member with a friction shoe at one end and an aperture at the other. The connection assembly also includes a housing. The housing has a passageway to receive a portion of the vertebral anchor and a bore to receive at least a portion of the shoe of the longitudinal member. The housing also includes a rod interface washer. The washer is positioned over the longitudinal member between the aperture of the longitudinal member and the face of the housing. The connection assembly further includes a compression member. The compression member is forceably, for example threadably, engageable into the aperture of the longitudinal member to urge the rod toward the vertebral anchor, whereby the shoe will be moved in the bore to urge the vertebral anchor toward the internal wall of the passageway in the housing, further pressing the housing and said rod interface washer together.

As used in this specification the term "shoe" means a structure that retards, stops, or controls the motion of another structure. WEBSTER'S NINTH NEW COLLEGIATE DICTIONARY 1088 (1990).

BREIF DESCRIPTION OF THE DRAWINGS

FIGS. 17 and 18 are perspective views of an embodiment of the invention.

FIGS. 21, 22 and 23 are respectively top, side and end views of a longitudinal member used in one embodiment of the invention.

FIGS. 24, 25 and 26 are respectively top, end and side views of a housing used in one embodiment of the invention.

DESCRIPTION OF THE PREFERRED EMBODIMENTS

Figure 1:
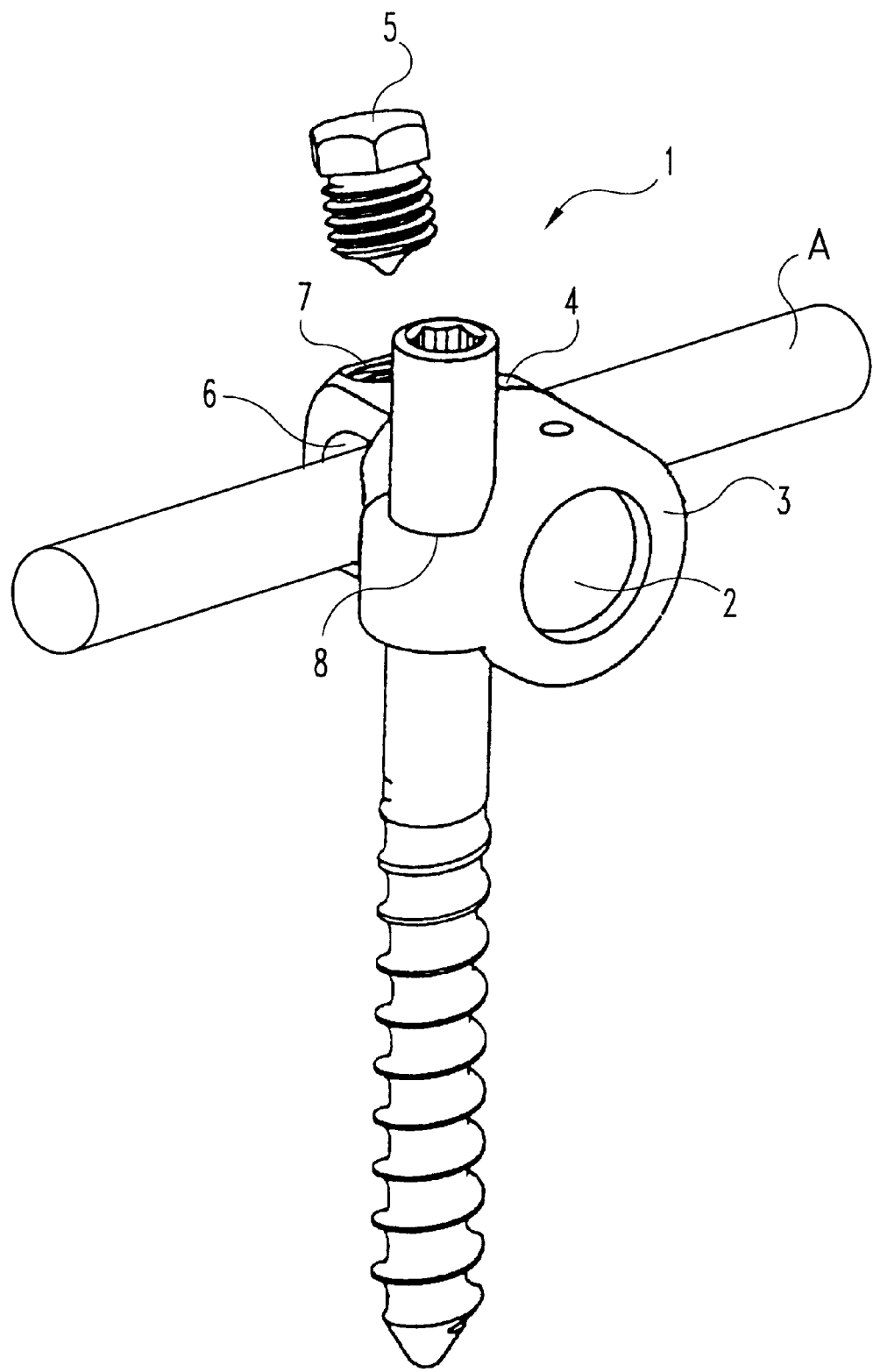
FIG. 1 is a perspective view of one embodiment of the present invention.
Figure 2:
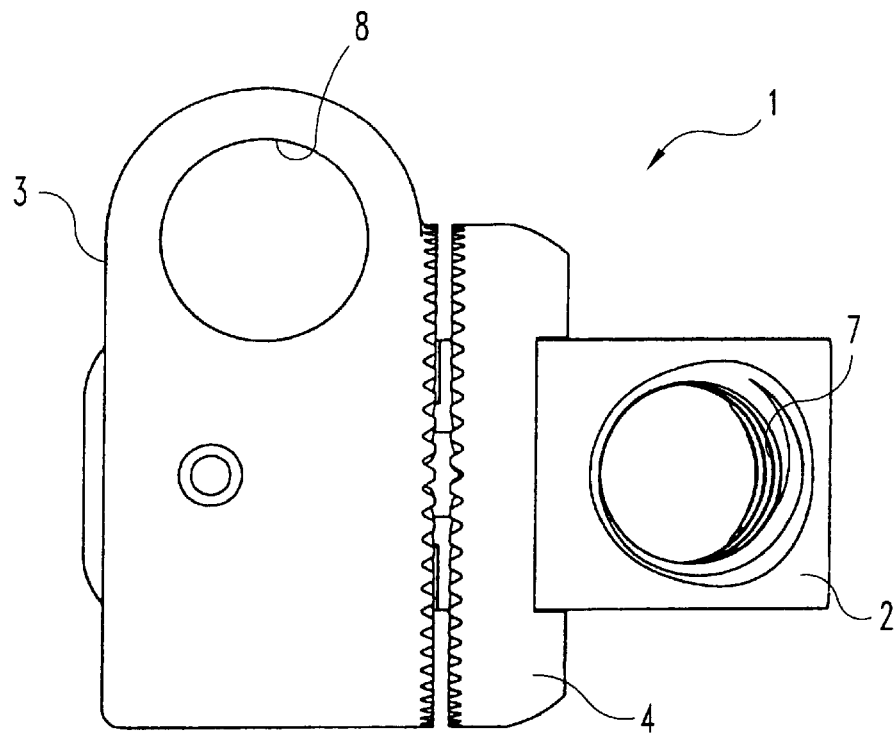
FIGS. 2 and 2A are top plan views of first and second embodiments of the invention.
Figure 3:
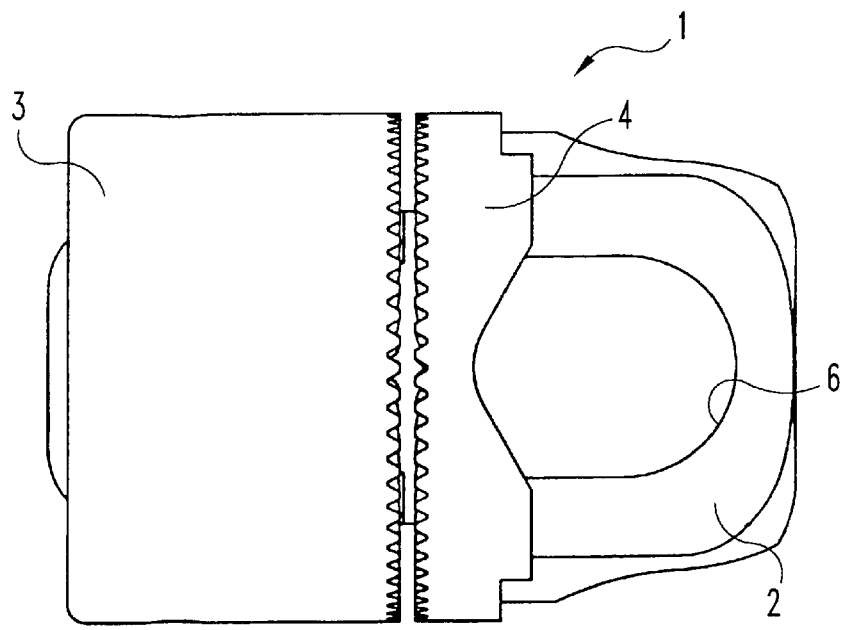
FIGS. 3 and 3A are side elevational views of first and second embodiments of the invention.
Figure 2A:
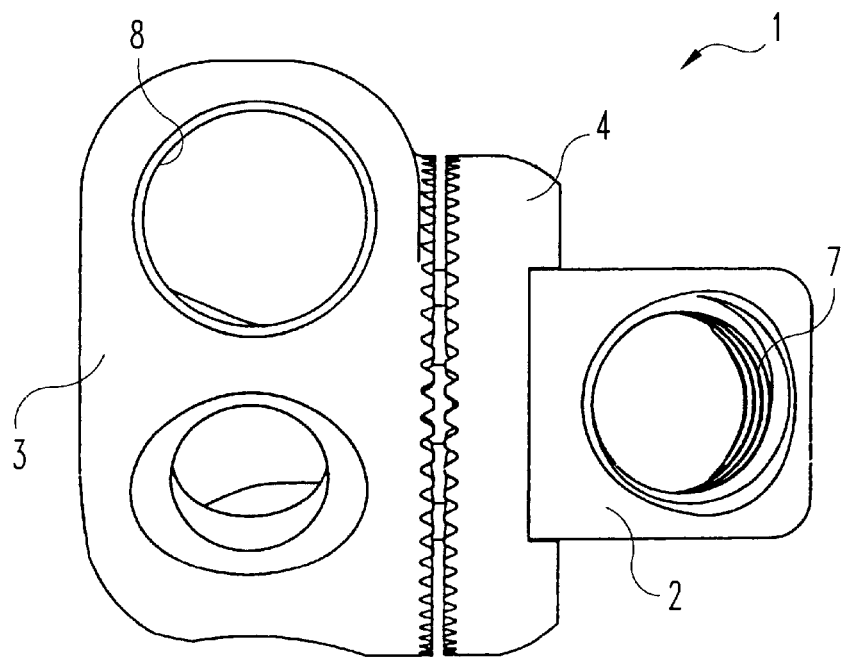
Figure 3A:
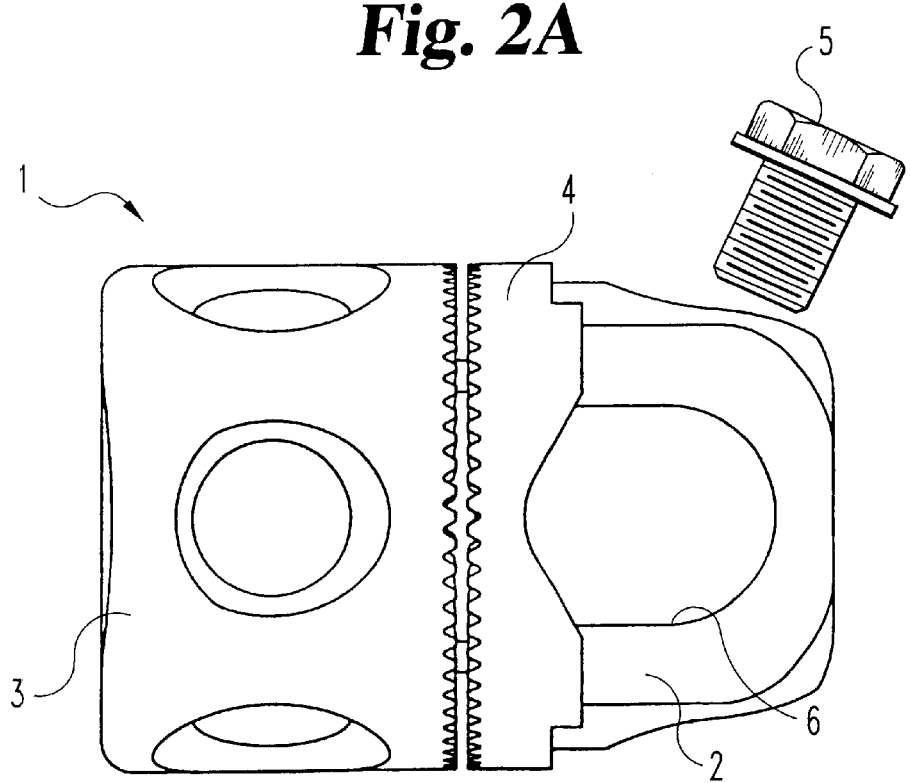

Specific language is used in the following description to publicly disclose the invention and to convey its principles to others. No limits on the breadth of the patent rights based simply on using specific language are intended. Also included are any alterations and modifications to the description that should normally occur to one of average skill in this technology.

A connection assembly 1 according to one embodiment of the invention is shown in FIGS. 1 to 4, and another embodiment of the invention is shown in FIGS. 2A to 4A. In either embodiment, connection assembly 1 includes a longitudinal member 2, a housing 3, and a rod interface washer 4. Longitudinal member 2 has an aperture 6 for receiving a rod "A" in a spinal implant system. While a closed aperture is shown, it will nevertheless be understood that an open-sided aperture may also be used to permit top-loading of the rod. And structure for urging the rod within the aperture 6, such as the set screw 5, is provided through a suitable threaded opening 7 in the longitudinal member 2 so as to be extendable into the aperture 6. The housing 3 has a passageway 8 for receiving a shaft or shank of a vertebral anchor "B" of a spinal implant system. Here again, while a closed passageway is shown, it will nevertheless be understood that an open-sided passageway may also be used.

Figure 6:
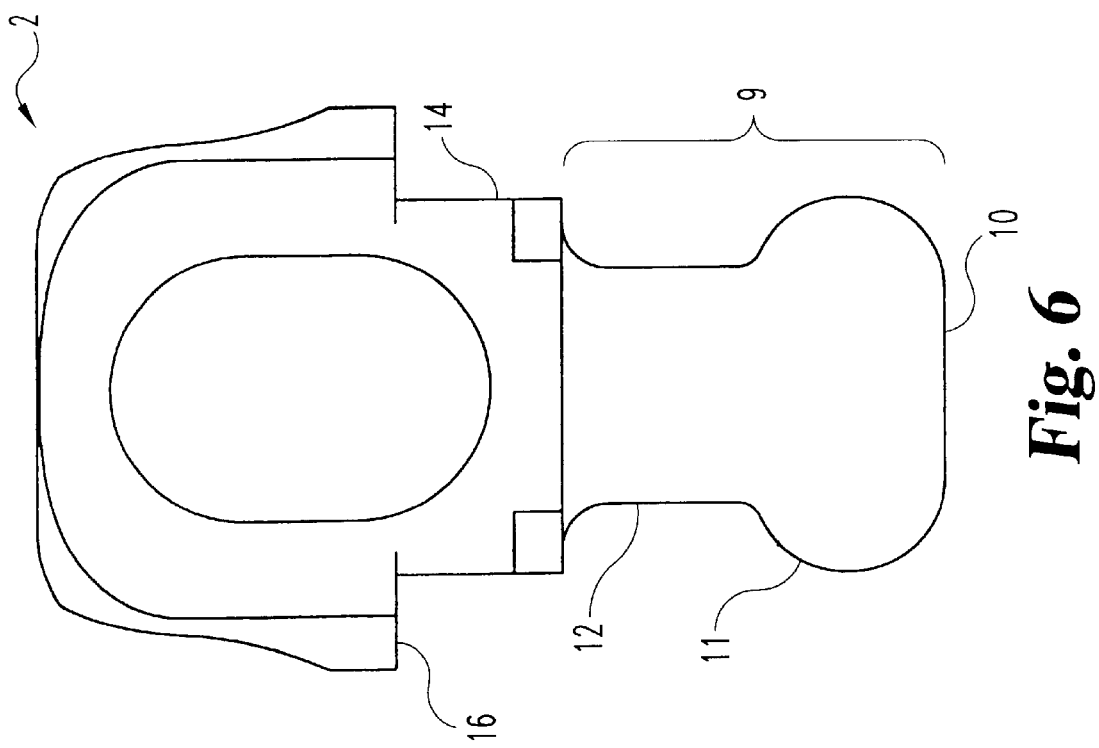
FIGS. 6 and 6A are side elevational views of a longitudinal member used in first and second embodiments of the invention.
Figure 5:
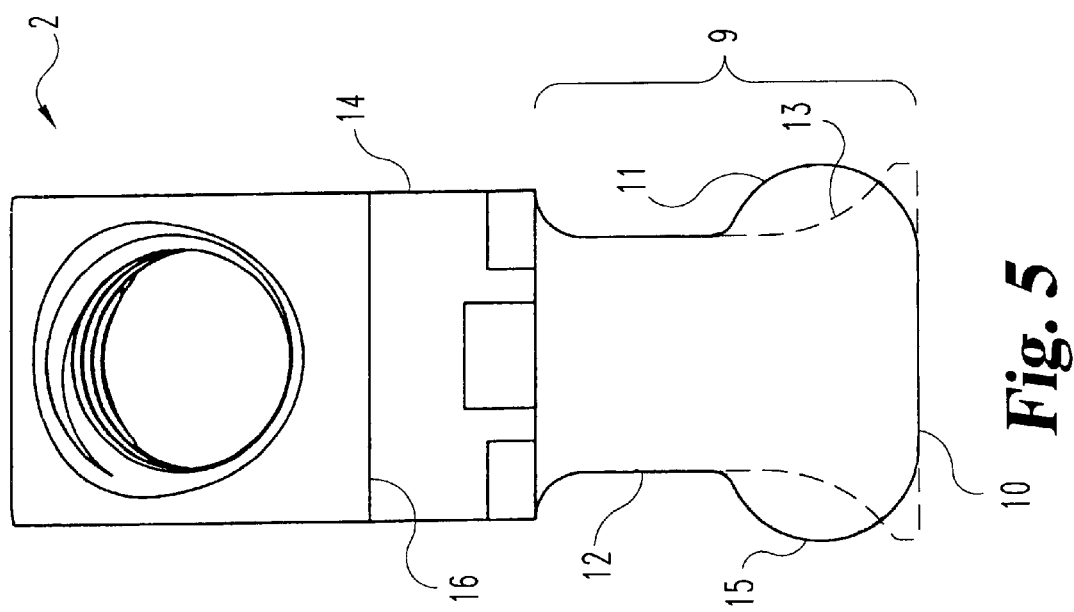
FIGS. 5 and 5A are top plan views of a longitudinal member used in first and second embodiments of the invention.
Figure 6A:
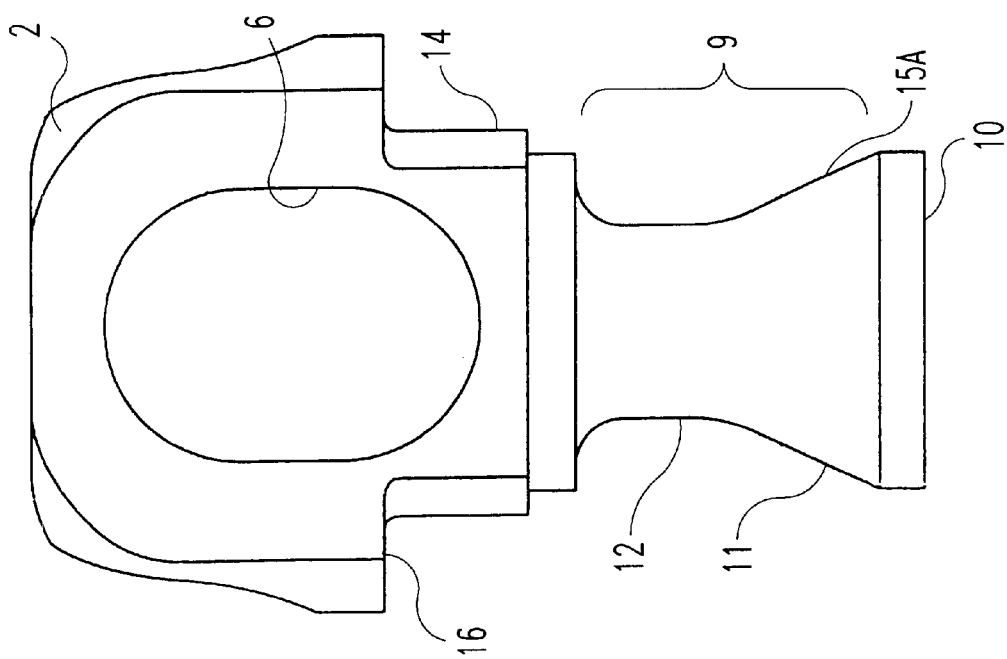
Figure 5A:
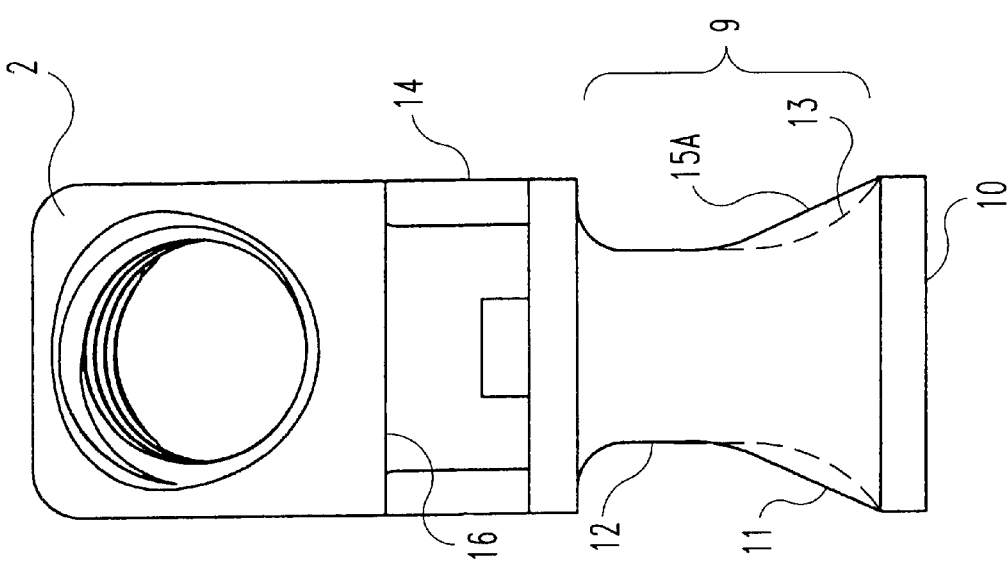
Figure 8:
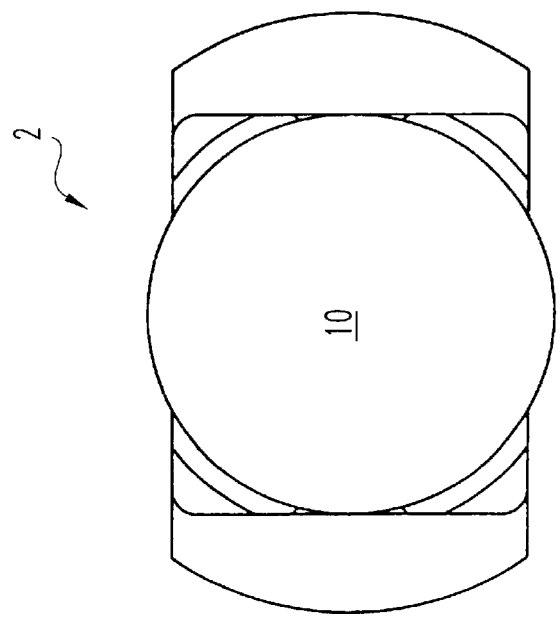
FIGS. 8 and 8A are end views of a longitudinal member used in first and second embodiments of the invention.
Figure 7:
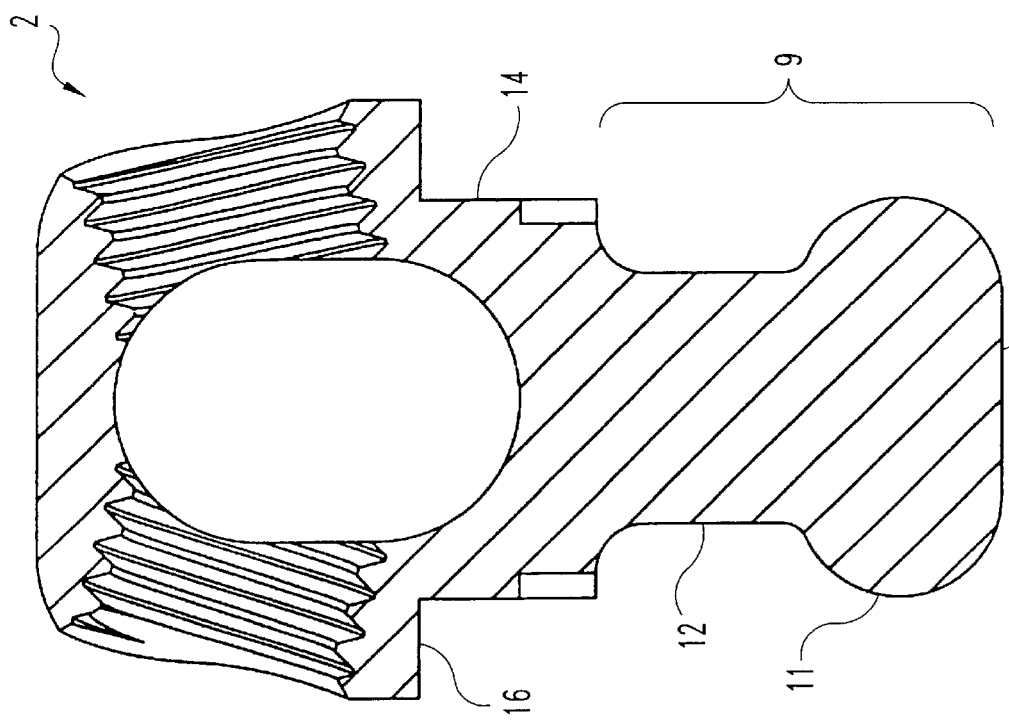
FIGS. 7 and 7A are side cross-sectional views of a longitudinal member used in first and second embodiments of the invention.
Figure 8A:
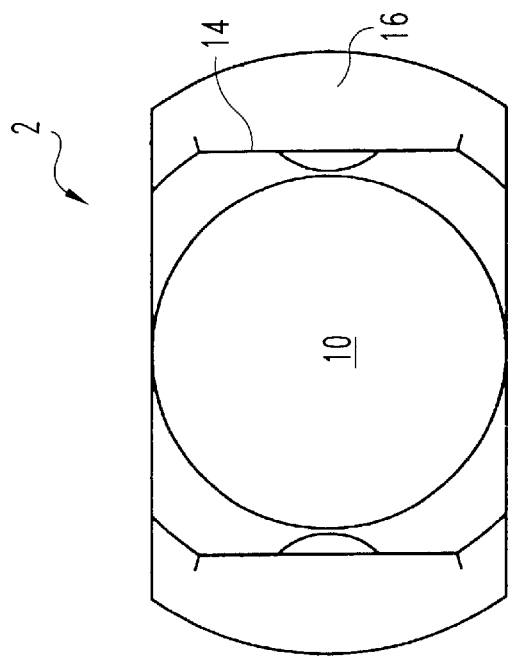
Figure 7A:
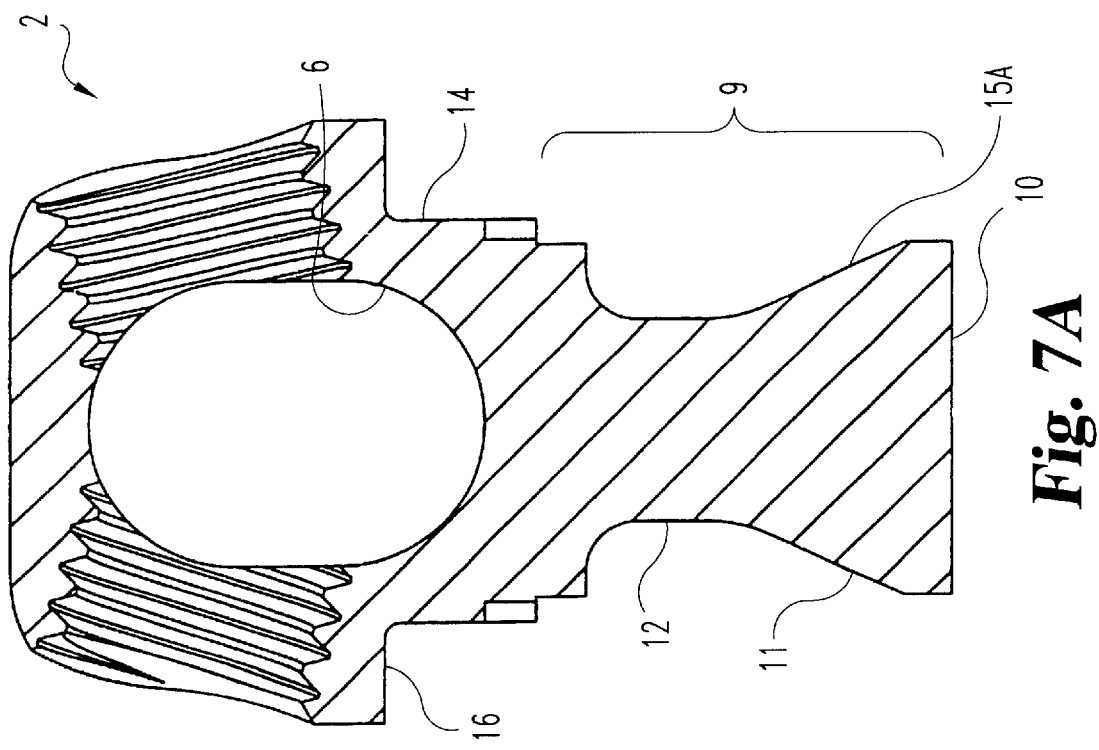
Figure 11:
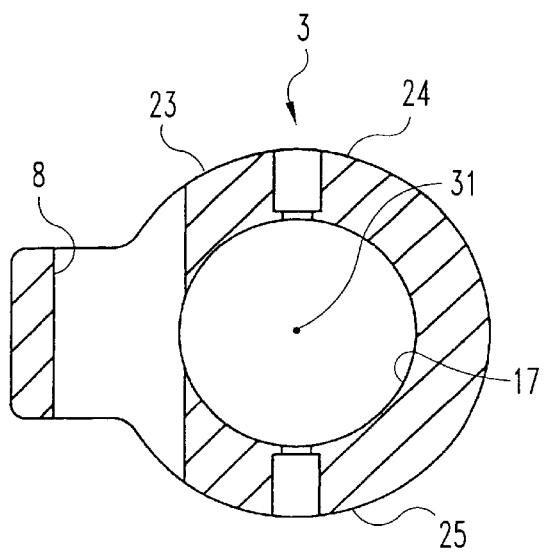
FIGS. 11 and 11A are axial cross-sectional views of a housing used in first and second embodiments of the invention.
Figure 9:
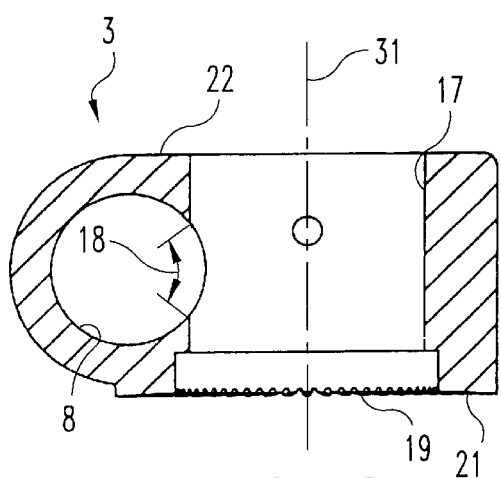
FIGS. 9 and 9A are top cross-sectional views of a housing used in first and second embodiments of the invention.
Figure 12:
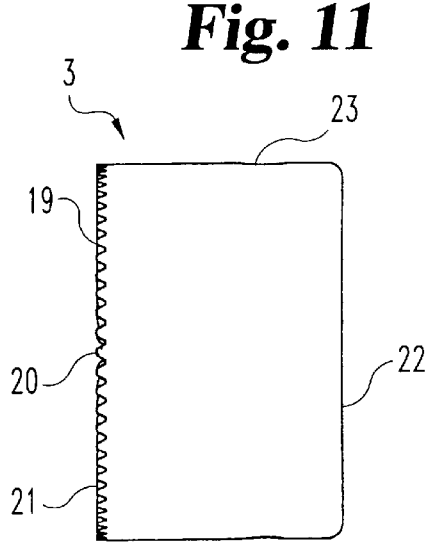
FIGS. 12 and 12A are end elevational views of a housing used in first and second embodiments of the invention.
Figure 9A:
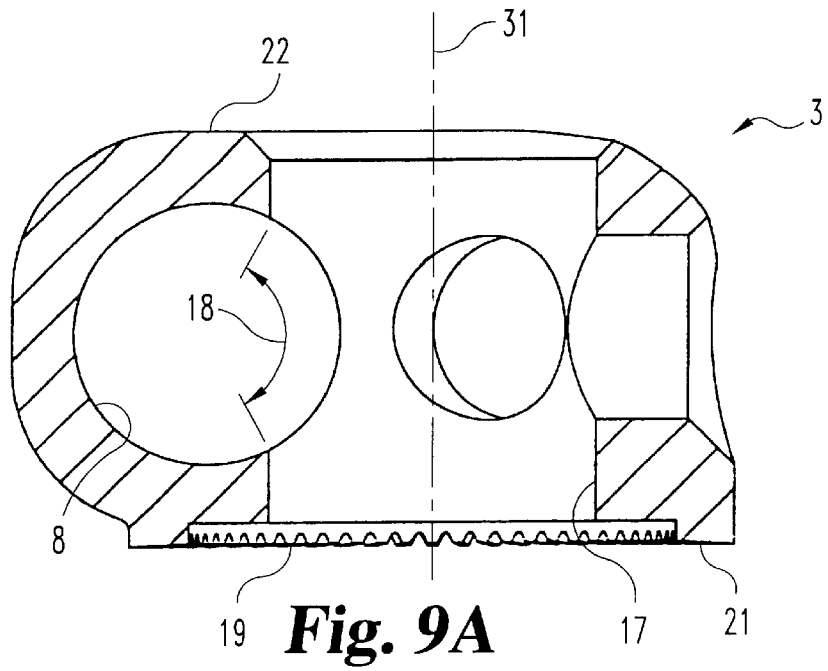

Additional details of longitudinal member 2 are shown in FIGS. 5 to 8 for one embodiment, and 5A to 8A for a second embodiment. Longitudinal member 2 has a friction shoe 9 near end 10. Friction shoe 9 has an inwardly tapered seat surface 11 that generally widens from neck portion 12 over the length of tapered seat surface 11 toward end 10. In FIGS. 5 to 7, the profile of tapered seat surface 11 is shown as generally convex our bulbous 15, however, other profiles are also contemplated by this invention. The practitioner of this invention may also use an inwardly tapered seat surface 11 with a generally concave profile 13 (dashed line in FIGS. 5 or 5A), which may, for example, resemble the profile of the flared bell on a trumpet. Or, the practitioner may use a tapered seat surface 11 with a generally straight profile 15A as shown FIGS. 5A to 7A or 15B in FIGS. 21 and 22. Above neck portion 12, longitudinal member 2 has a washer seat portion 14. A washer seat portion 14 that is substantially rectangular in cross-section, optionally with rounded corners, is currently preferred, but washer seat portion 14 can largely be of any suitable shape. Above washer seat portion 14, longitudinal member 2 has a washer stop surface 16. Washer stop surface 16 can be provided in longitudinal member 2, as shown, by providing an enlarged portion of the longitudinal member 2 next to washer seat portion 14.

Figure 10:
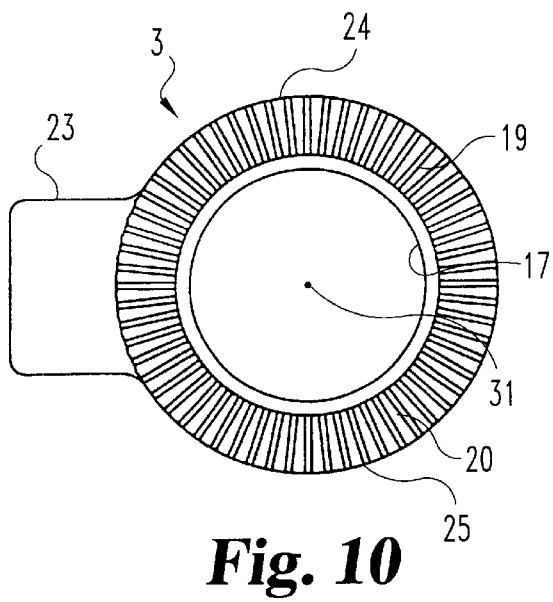
FIGS. 10 and 10A are bottom plan views of a housing used in first and second embodiments of the invention.
Figure 10A:
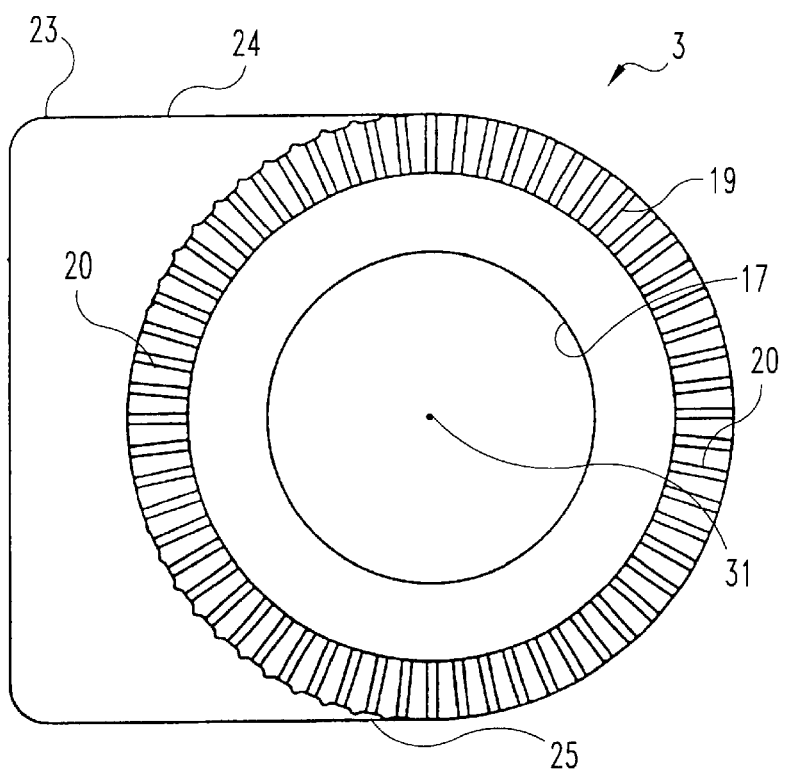
Figure 11A:
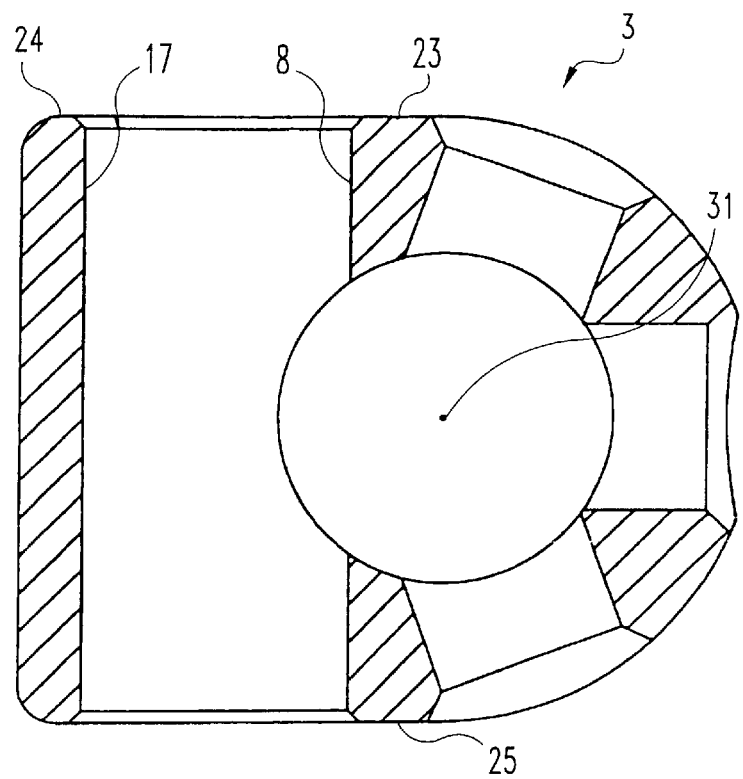
Figure 12A:
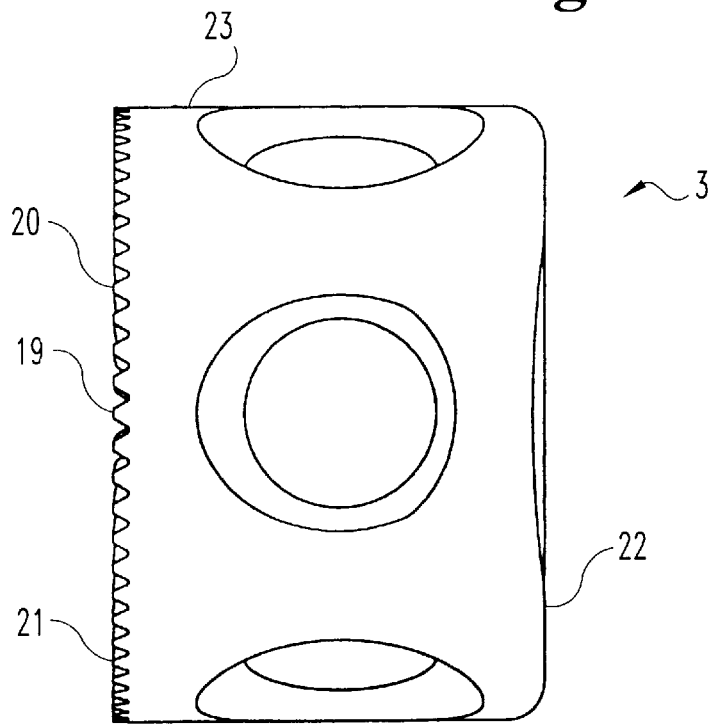

Additional details of housing 3 are shown in FIGS. 9 to 12 for one embodiment, and FIGS. 9A to 12A for a second embodiment. Housing 3 can be any of several suitable shapes, including the general round shape depicted in FIG. 10 or the general "D"-shape depicted in FIG. 10A. Housing 3 has a passageway 8 in its lateral edge 23 that is open between the top 24 of housing 3 and the bottom 25 of housing 3. Passageway 8 is sized to accept the shank of a vertebral anchor. Housing 3 also has a bore 17 that is preferably open between faces 21 and 22 of housing 3. Bore 17 is sized to accept the frictional shoe 9 of longitudinal member 2. Bore 17 is open to passageway 8 along radius 18, such that the shaft of vertebral anchor "B" placed inside passageway 8 partially extends into bore 17. One face of housing 3 has a washer connection surface 19. Washer connection surface 19 preferably includes structure for facilitating the engagement of housing 3 against rotational movement relative to the rod interface washer 4 against which it is pressed. This engagement structure is preferably a plurality of variable angle ridges 20 that radiate from the axis 31 of bore 17.

Figure 16:
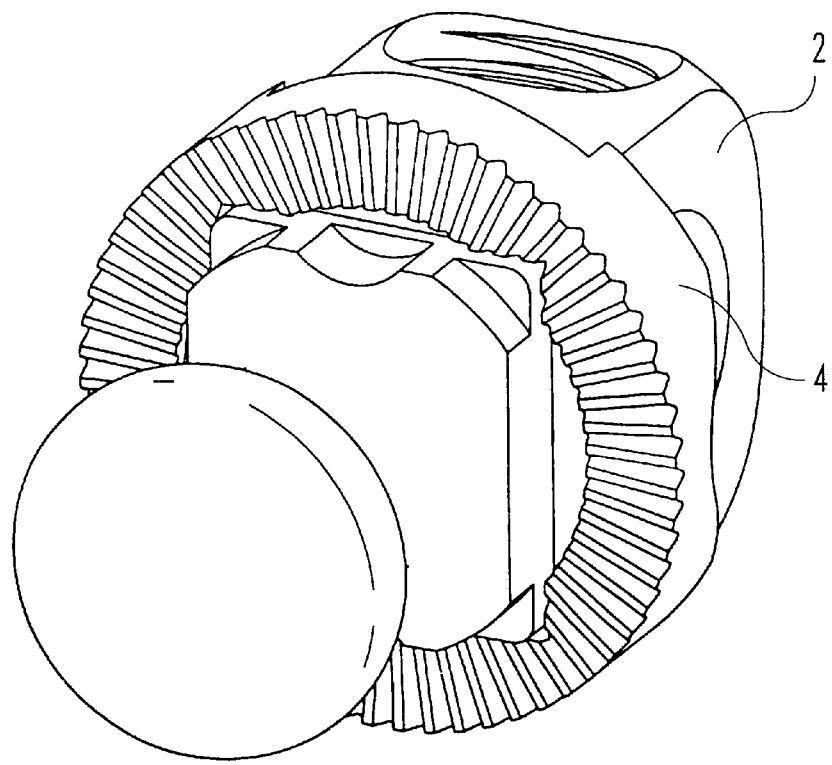
FIGS. 16 and 16A are perspective views of a longitudinal member and rod interface washer used in first and second embodiments of the invention.
Figure 16A:
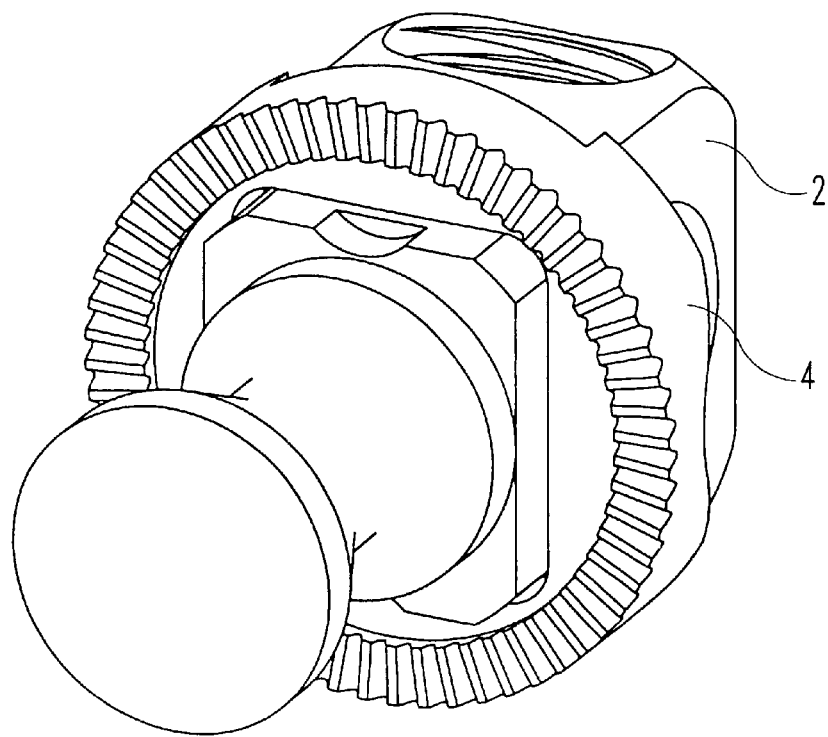
Figure 14:
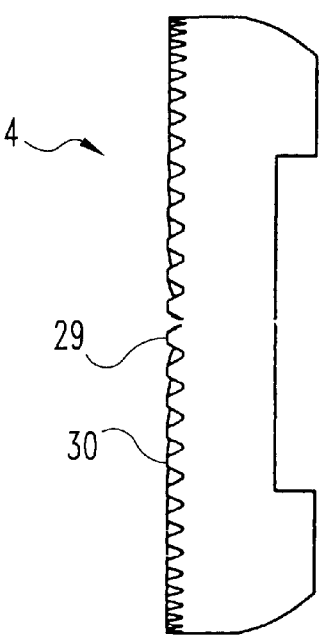
FIGS. 14 and 14A are side views of a rod interface washer used in first and second embodiments of the invention.
Figure 13:
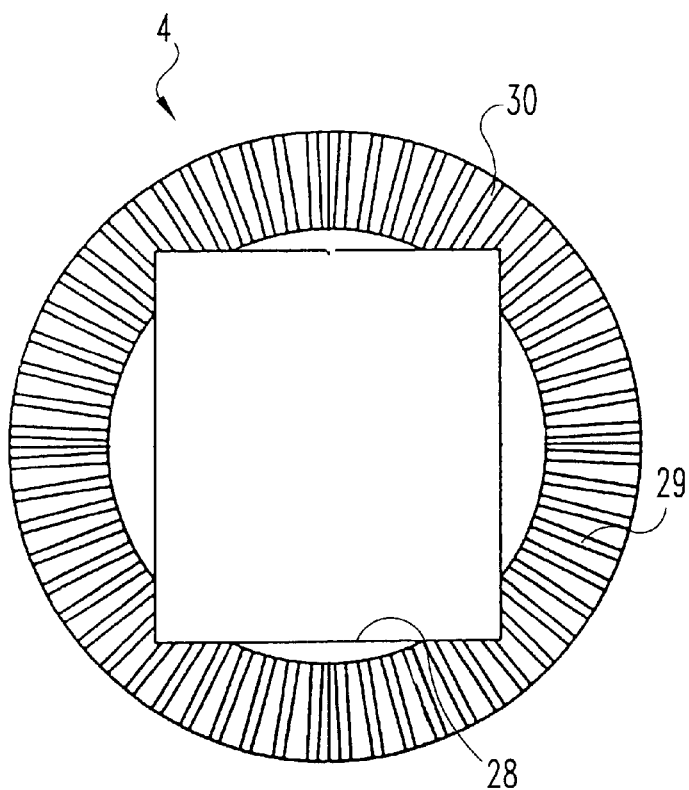
FIGS. 13 and 13A are bottom plan views of a rod interface washer used in first and second embodiments of the invention.
Figure 15:
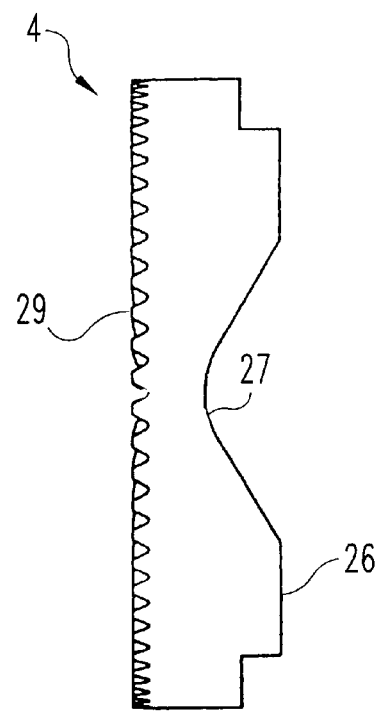
FIGS. 15 and 15A are end views of a rod interface washer used in first and second embodiments of the invention.
Figure 14A:
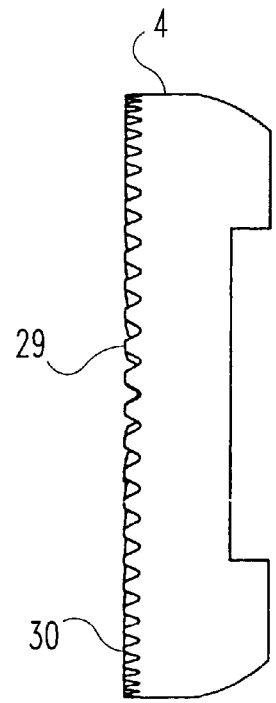
Figure 13A:
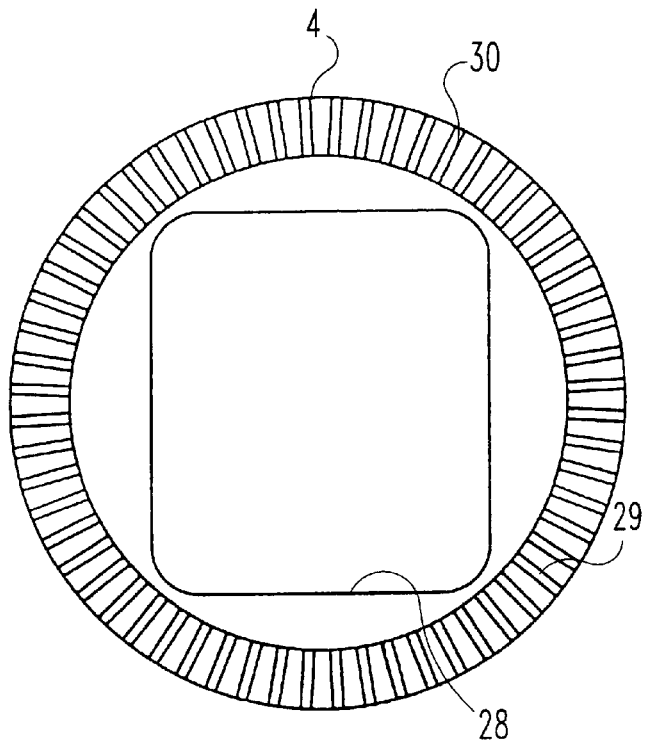
Figure 15A:
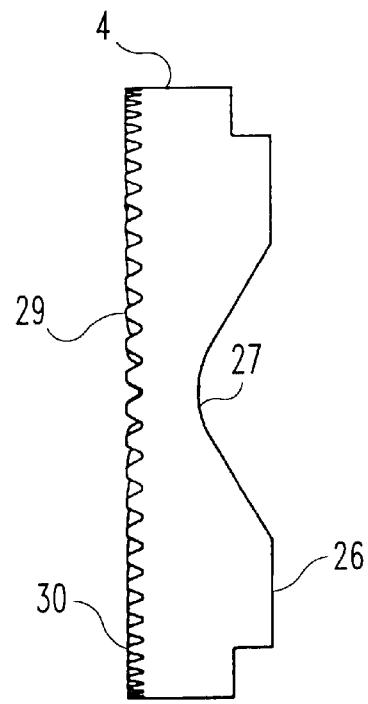

Details of rod interface washer 4 are shown in FIGS. 13 to 14 for one embodiment and FIGS. 13A to 14A for a second embodiment. The interface washer can be any of several suitable shapes, including the circular shapes that are depicted. One surface of rod interface washer 4 has an engagement surface 26, which preferably has an engagement groove 27 for engaging a cylindrical rod. The engagement groove 27 runs substantially diametrically through the washer. A central opening 28 in the washer corresponds in shape to the cross-sectional shape of the washer seat 14 of longitudinal member 2 to which it is engaged (FIG. 16 and FIG. 16A). In the currently preferred embodiments, the corresponding openings and washer seats are of substantially rectangular shape, although the actual shape and size could vary.

The rod interface washer 4 has a housing connection surface 29 opposite the engagement surface 27. The housing connection surface 29 preferably includes structure for facilitating the engagement of the washer against rotational movement relative to the housing 3 against which it is pressed. This engagement structure is preferably a plurality of variable angle ridges 30, which radiate from the rotational center of the rod interface washer 4.

Figure 4:
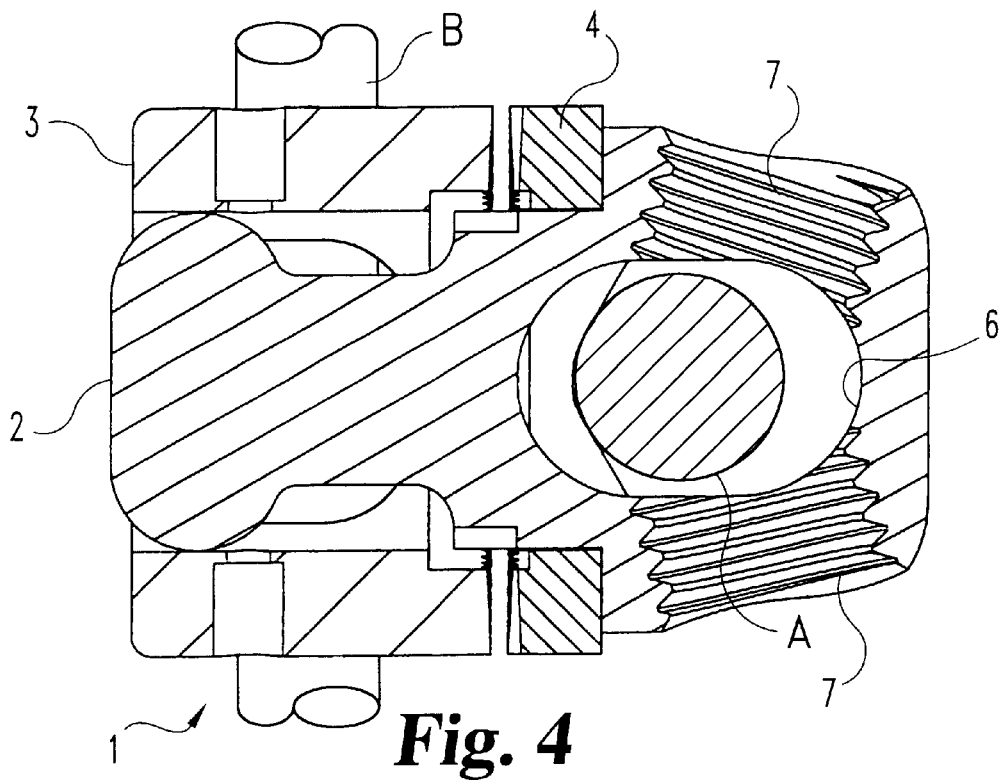
FIGS. 4 and 4A are side cross-sectional views of first and second embodiments of the invention.
Figure 4A:
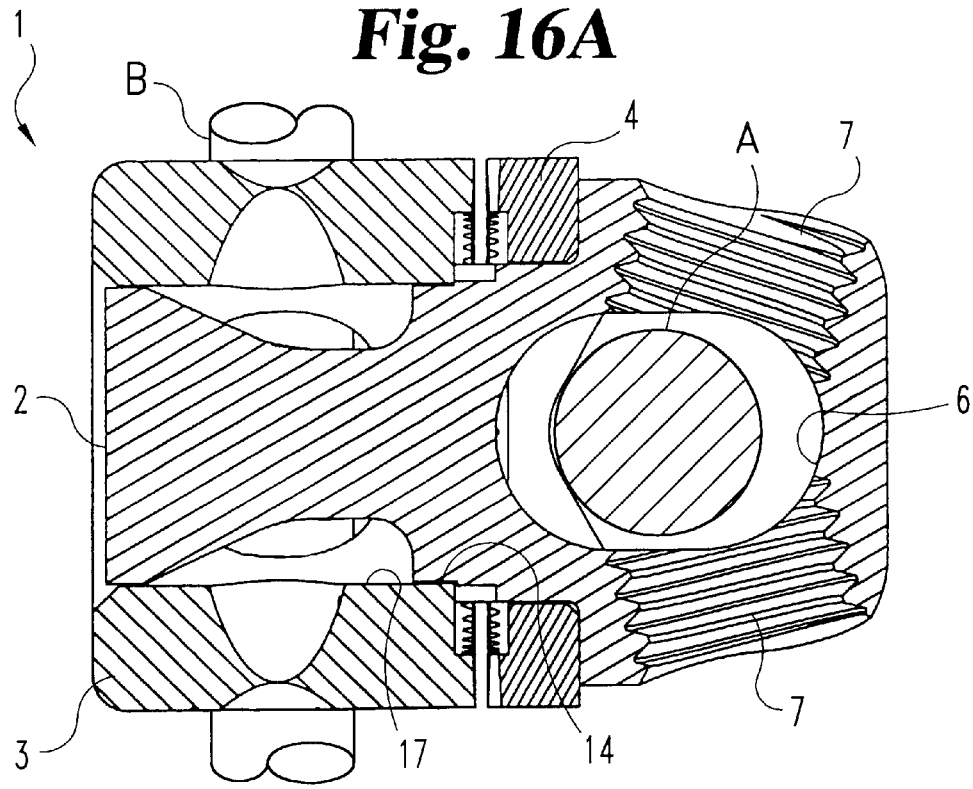

The rotable connection assembly and its manner of assembly are shown in cross-section in FIG. 4 for one embodiment and FIG. 4A for a second embodiment. A rod "A" is positioned in the aperture 6 of longitudinal member 2. The post or shaft of a vertebral anchor "B" is positioned through passageway 8 of housing 3. It will be appreciated that the vertebral anchor "B" is typically oriented somewhat vertically into the spine when the patient is lying horizontally, and that the rod "A" extends somewhat horizontally along the length of spine of the patient, again when the patient is lying.

Housing 3 and rod interface washer 4 are positioned on longitudinal member 2. Rod interface washer 4 rides over washer seat portion 14 of longitudinal member 2 (FIGS. 16 and 16A) and shoe 9 is inserted inside bore 17 of housing 3. The housing connection surface 29 of rod interface washer 4 faces the washer connection surface 19 of housing 3 in the completed assembly, which allows the variable angle surfaces 20 and 30 to be placed together, permitting mutual engagement of the two surfaces.

Longitudinal member 2 is generally held in housing 2 by the insertion of the shank of a vertebral anchor "B" into passageway 8. When the shank is inserted into passageway 8, the frictional shoe 9 can no longer be removed from bore 17. A portion of the shank extends into bore 17 between end 10 and aperture 6, and pulling longitudinal member out of bore 17 places inwardly tapered seat surface 11 in contact with the shank of vertebral anchor "B", preventing longitudinal member 2 from being further removed.

As a result of this arrangement, connection assembly 1 may be tightened to rod "A" and vertebral anchor "B" by threading compression member 5 into threaded opening 7. Threading compression member 5 into opening 7 clamps rod "A" between rod interface washer 4 and compression member 5. This action, in turn, interlocks connection surfaces 19 and 29 and pulls frictional shoe 9 from bore 17. Pulling frictional shoe 9 from bore 17 clamps the shank of vertebral anchor "B" between the side wall of passageway 8 and the inwardly tapered seat surface 11 of shoe 9, locking the entire connection assembly against movement. Adjustments are then made loosening set screw 5 and then retightening the set screw when the preferred position has been located.

Several details should now be noted. First, the width of housing 3 and rod interface washer 4 is such that when connection assembly 1 is loaded, but not tightened, onto a rod and vertebral anchor, there is some freedom of movement of housing 3 and washer 4 over longitudinal member 2. And preferably, this freedom of movement is sufficient to allow washer connection surface 19 and housing connection surface 29 to slide past each other. Second, the aperture 6 of longitudinal member 2 and passageway 8 of housing 3 are larger in dimension than the cross-section of the rod "A" or vertebral anchor "B", such that movement of each within their respective openings is possible. And third, it is generally preferable that washer seat portion 14 be of sufficient length and width to ride on bore 17 when connection assembly has not yet been tightened to a rod and vertebral anchor. In some applications, this may increase the ease with which connection assembly 1 can be tightened.

So being, the connection assembly 1 can be readily located most anywhere on a spinal rod, can be readily located most anywhere over the shank of a vertebral anchor, and connection assembly 1 can accommodate most any angle between the rod and the vertebral anchor. Additional details of the installation of such vertebral anchors and advantages of such multiple adjustments in the X, Y, and Z planes can be found in U.S. Pat. Nos. 5,643,263 and 5,885,285 to Simonson, the disclosures of which being specifically incorporated into this specification by reference.

Figure 17:
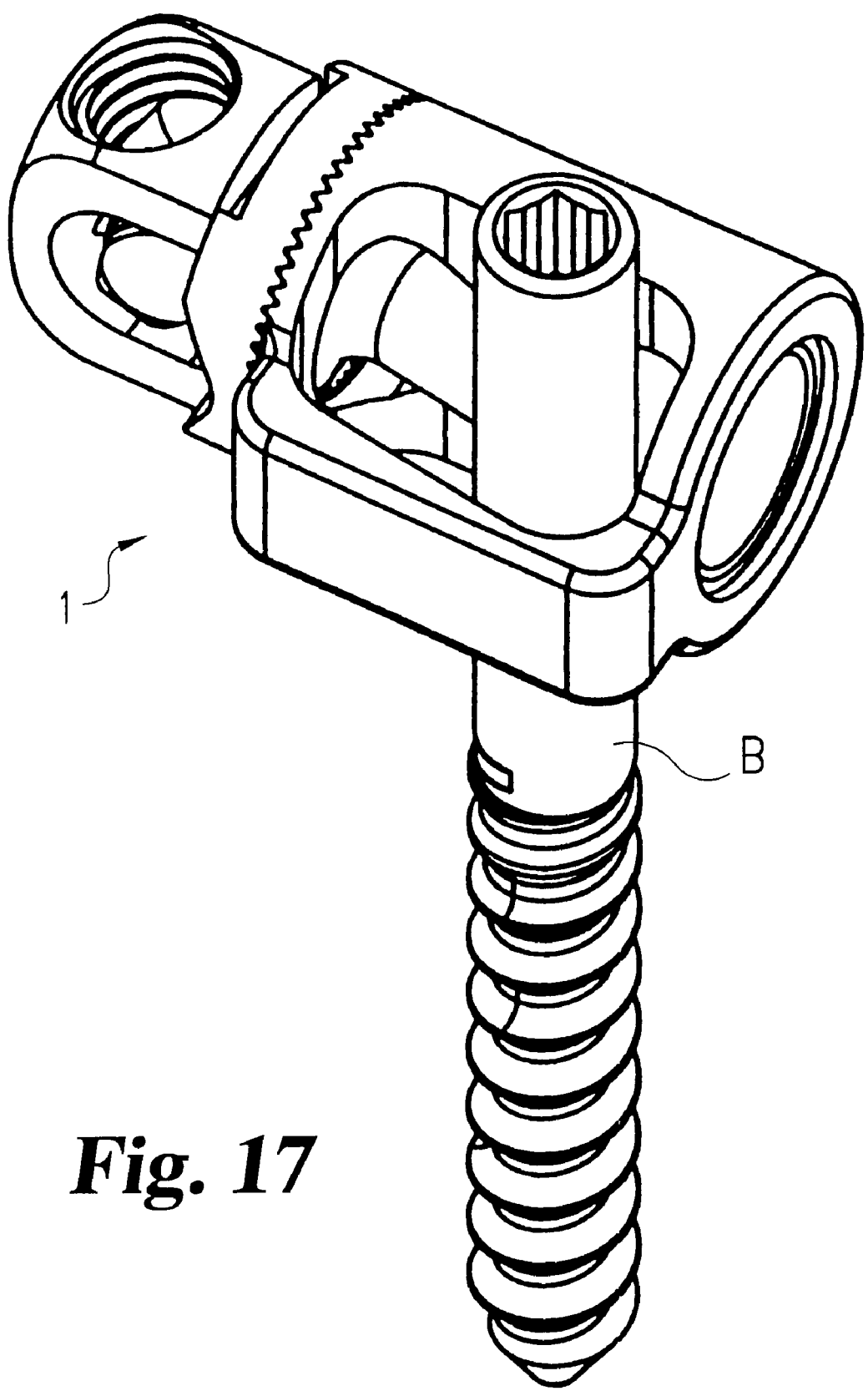
Figure 19:
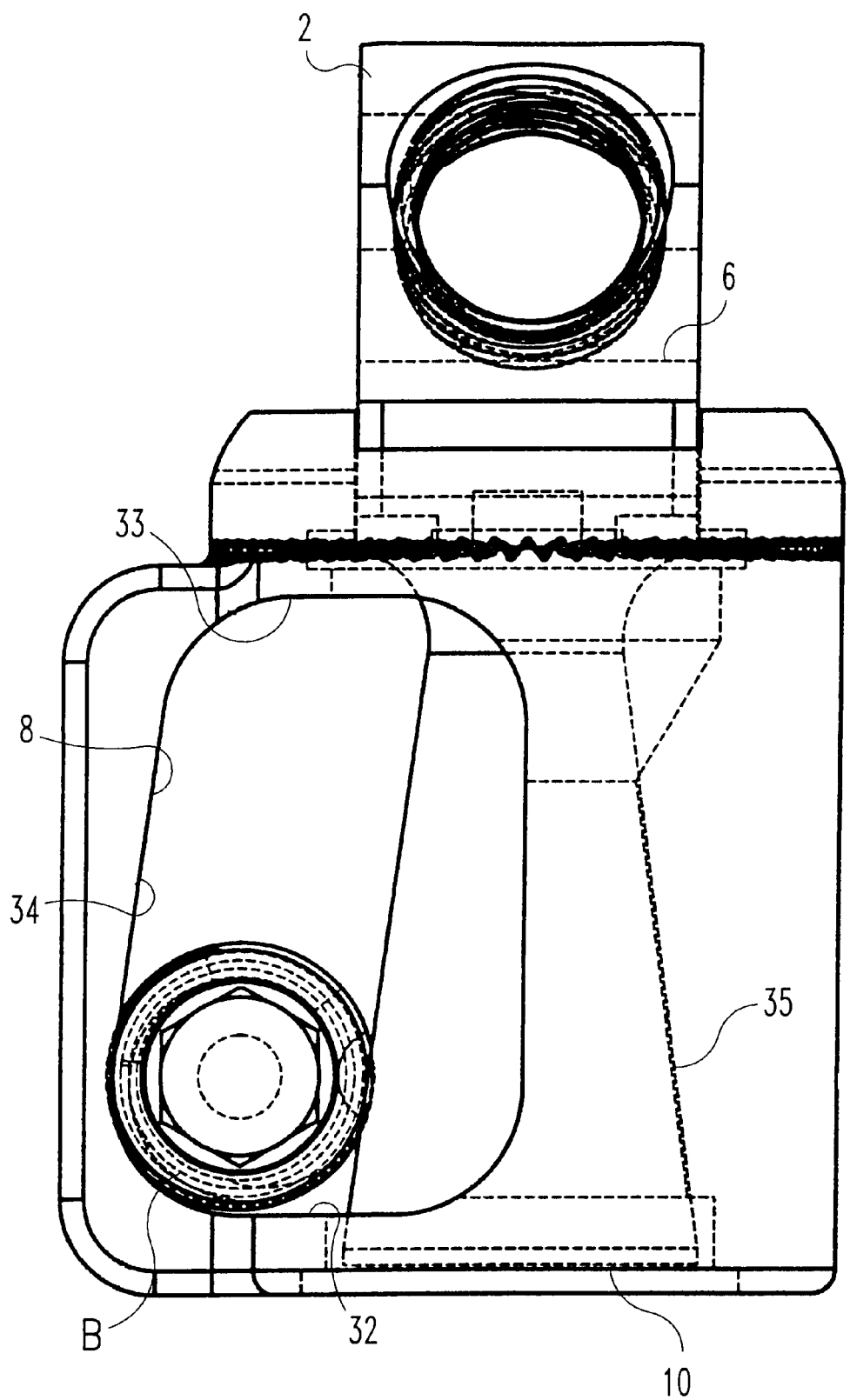
FIGS. 19 and 20 are plan views of an embodiment of the invention.
Figure 20:
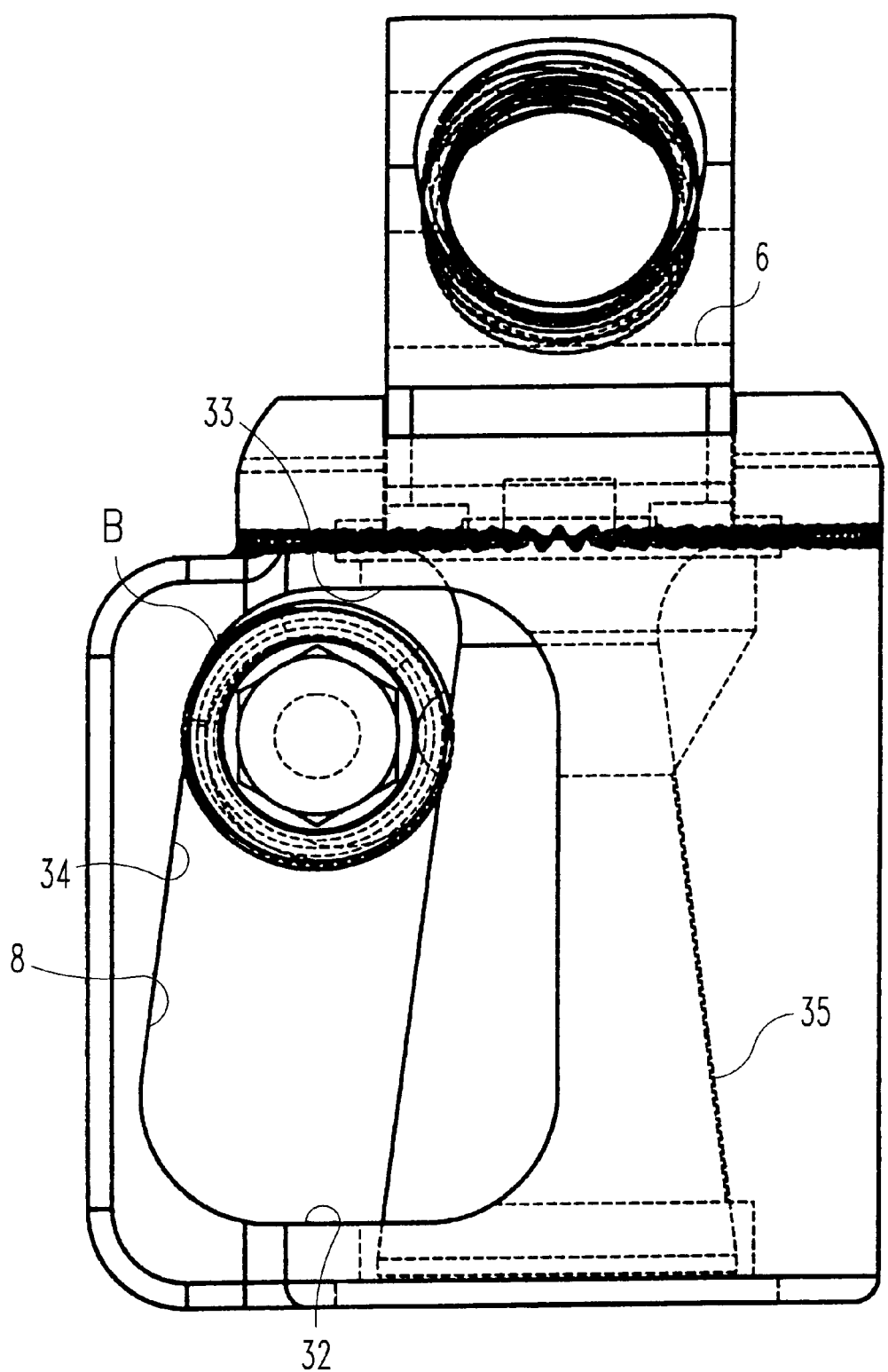

Yet another alternative embodiment of connection assembly 1 is shown in FIG. 17. As with the previous embodiments and referring to FIG. 18, this version also includes a longitudinal member 2, a housing 3, and a rod interface washer 4. This embodiment, however, has an elongated passageway 8, which allows the surgeon to variably fix the distance between vertebral anchor "B" and a rod residing in aperture 6. Compare FIGS. 19 and 20. Vertebral anchor "B" can be clamped in passageway 8 near end 32, can be clamped in passageway 8 near end 33, or anchor "B" can be clamped in passageway 8 at any location between ends 32 and 33.

Additional details of longitudinal member 2 of this embodiment are shown in FIGS. 21 to 23. Again, longitudinal member 2 has an aperture 6 for receiving a spinal implant rod and a threaded opening 7 for receiving a setscrew. And also again, longitudinal member 2 has a friction shoe 9 near end 10. Friction shoe 9 has an inwardly tapered seat surface 11 that generally widens from neck portion 12 over the length of tapered seat surface 11 toward end 10. In FIGS. 21 to 23, the profile of tapered seat surface 11 has a generally straight profile 15B, however, this embodiment may also incorporate the previously described convex or concave profiles. Above neck portion 12, longitudinal member 2 has a washer seat portion 14. A washer seat portion 14 that is substantially rectangular in cross-section, optionally with rounded corners, is currently preferred, but washer seat portion 14 can largely be of any suitable shape. Above washer seat portion 14, longitudinal member 2 has a washer stop surface 16. Washer stop surface 16 can be provided in longitudinal member 2, as shown, by providing an enlarged portion of the longitudinal member 2 next to washer seat portion 14.

Additional details of housing 3 of this embodiment are shown in FIGS. 24 to 25. As previously described, housing 3 has a passageway 8 in its lateral edge 23 that is open between the top 24 of housing 3 and the bottom 25 of housing 3. Passageway 8 has sufficient width to accept the shank of a vertebral anchor. Housing 3 also has a bore 17 that is preferably open between faces 21 and 22 of housing 3. Bore 17 is sized to accept the frictional shoe 9 of longitudinal member 2, and bore 17 is open to passageway 8 (FIGS. 19 or 20), such that the shaft of vertebral anchor "B" placed inside passageway 8 partially extends into bore 17. One face of housing 3 has a washer connection surface 19. Washer connection surface 19 preferably includes structure for facilitating the engagement of housing 3 against rotational movement relative to the rod interface washer 4 against which it is pressed. This engagement structure is preferably a plurality of variable angle ridges 20 that radiate from the axis 31 of bore 17.

In contrast to the previous embodiments of this invention and referring back to FIGS. 19 and 20, the reader may note the longer length of frictional shoe 9, the elongated shape of passageway 8, and the partial internal taper of bore 17. Passageway 8 is elongated to provide for adjustable fixation of the vertebral anchor "B" along the length of shoe 9. To assist in this result, it is preferable that lateral wall 34 of passageway 8 be tapered to complement the taper of inwardly tapered seat surface 11 on shoe 9. Provided in this manner, substantially the same amount of axial displacement of longitudinal member 2 from bore 17 will lock vertebral anchor "B" at any location inside passageway 8. Moreover, to minimize the amount of axial displacement required to lock vertebral anchor "B", it is further preferable that side wall 35 also be tapered so as to push shoe 9 against vertebral anchor "B" when longitudinal member 9 is axially displaced. And preferably, the taper inside wall 35 is such that it too complements the taper of inwardly tapered seat surface 11 as lateral wall 34 preferably does.

Figure 27:
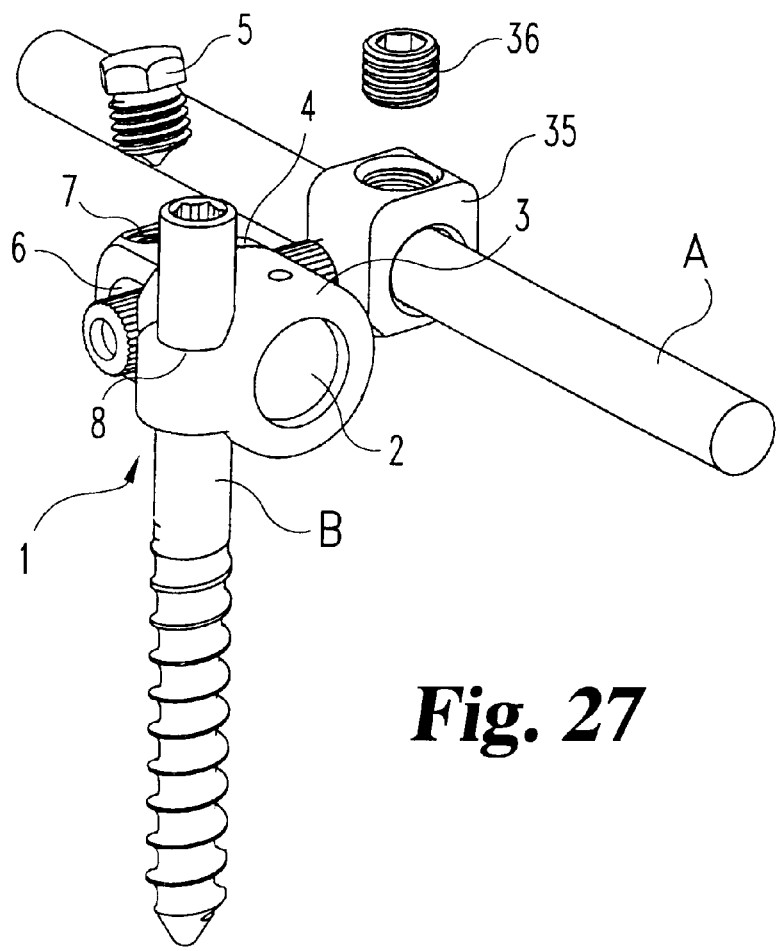
FIG. 27 is a perspective view of one embodiment of the invention.
Figure 28:
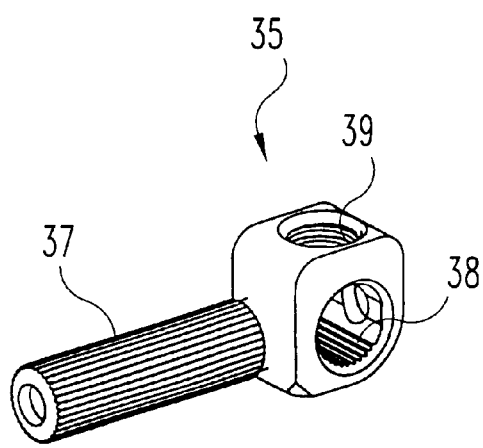
FIG. 28 is a perspective view of a spindle used in one embodiment of the invention.

Yet another alternative embodiment of this invention is shown in FIG. 27. In this embodiment, any of the foregoing connection assemblies 1 is used with an offset connector or spindle 35 and a compression member 36. Referring to FIG. 28, spindle 35 has a generally cylindrical projection portion or shaft 37, a hole 30 for receiving a spinal implant rod, and a threaded opening 39 for receiving compression member 36. The length of projection portion 37 is preferably roughened or scored, as well as the walls of hole 30. An example of such an offset connector or spindle is commercially available as part of the LIBERTY™ system offered by Medtronic Sofamor Danek located in Memphis, Tennessee, U.S.A.

Instead of attaching connection assembly 1 directly to spinal implant rod "A", spindle 35 is attached to rod "A" and secured by compression member 36. Connection assembly 1 is then secured to the offset connector by inserting projection portion 37 into aperture 6 and tightening connector assembly 1 as previously described.

While the invention has been illustrated and described in detail, this is to be considered illustrative and not restrictive of the patent rights. The reader should understand that only the preferred embodiments have been presented and all changes and modifications that come within the spirit of the invention are included if the following claims or the legal equivalent of these claims describes them.

What is claimed is:

1. A connection assembly between a spinal implant rod and a vertebral anchor, the assembly comprising:
   (a) a longitudinal member, said longitudinal member having a shoe disposed near one end of the longitudinal member and an aperture for receiving a portion of the spinal implant rod near the opposite end of the longitudinal member;
   (b) a housing, said housing having a first face, a second face, and a lateral edge, said housing having a passageway opening to the lateral edge to receive a portion of the vertebral anchor, the passageway having an internal wall, said housing having a bore opening to the first face to receive at least a portion of the shoe of said longitudinal member, said housing being movable in part over at least a portion of the shoe of said longitudinal member, the passageway further open to the bore;
   (c) a rod interface washer, said rod interface washer positioned over a portion of the longitudinal member between the aperture of said longitudinal member and the first face of said housing, said rod interface washer being movable in part between the aperture of said longitudinal member and said housing, said rod interface washer being fixed against rotation relative to said longitudinal member;
   (d) a compression member, said compression member forceably engaged to said longitudinal member to urge the rod toward the vertebral anchor, whereby the shoe will be moved in the bore to urge the vertebral anchor toward the internal wall of the passageway in said housing, and whereby said housing and said rod interface washer will be pressed together.

2. The connection assembly of claim 1, wherein the shoe of said longitudinal member is a wedge.

3. The connection assembly of claim 1, wherein the shoe of said longitudinal member has a round cross-section.

4. The connection assembly of claim 1, wherein the shoe of said longitudinal member is conical shaped.

5. The connection assembly of claim 1, wherein the shoe of said longitudinal has a convex taper.

6. The connection assembly of claim 1, wherein the shoe of said longitudinal member has a concave taper.

7. The connection assembly of claim 1, wherein the shoe of said longitudinal member has a substantially straight taper.

8. The connection assembly of claim 1, wherein said housing and said rod interface washer have interengagement structure on a surface such that, when pressed together, the interengagement structure will facilitate against rotational movement relative to one another.

9. The connection assembly of claim 1, wherein the shoe of said longitudinal member is tapered and the shoe has a lateral edge.

10. The connection assembly of claim 9, wherein the passageway is a slot and at least a portion of the internal wall of the slot is substantially parallel with at least a portion of the lateral edge of the shoe of said longitudinal member.

11. The connection assembly of claim 9, wherein at least a portion of the bore in said housing is complementary tapered to mate with at least a portion of the taper of the shoe of said longitudinal member.

12. The connection assembly of claim 9, wherein the shoe of said longitudinal member has a substantially straight taper.

13. The connection assembly of claim 1, wherein the bore of said longitudinal member opens to the first face and the second face of said housing.

14. A connection assembly between a spinal implant rod and a vertebral anchor, the assembly comprising:

(a) a spindle, said spindle having an aperture for receiving a portion of the spinal implant rod, said spindle having a projection portion;

(b) a longitudinal member, said longitudinal member having a shoe disposed near one end of the longitudinal member and an aperture for receiving a portion of the projection portion of said spindle;

(c) a housing, said housing having a first face, a second face, and a lateral edge, said housing having a passageway opening to the lateral edge to receive a portion of the vertebral anchor, the passageway having an internal wall, said housing having a bore opening to the first face to receive at least a portion of the shoe of said longitudinal member, said housing being movable in part over at least a portion of the shoe of said longitudinal member, the passageway further open to the bore;

(d) a rod interface washer, said rod interface washer positioned over a portion of the longitudinal member between the aperture of said longitudinal member and the first face of said housing, said rod interface washer being movable in part between the aperture of said longitudinal member and said housing, said rod interface washer being fixed against rotation relative to said longitudinal member;

(e) a compression member, said compression member forceably engaged to said longitudinal member to urge the rod toward the vertebral anchor, whereby the shoe will be moved in the bore to urge the projection portion of said spindle toward the internal wall of the passageway in said housing, and whereby said housing and said rod interface washer will be pressed together.

15. The connection assembly of claim 14, wherein the shoe of said longitudinal member is a wedge.

16. The connection assembly of claim 14, wherein the shoe of said longitudinal member has a round cross-section.

17. The connection assembly of claim 14, wherein the shoe of said longitudinal member is conical shaped.

18. The connection assembly of claim 14, wherein the shoe of said longitudinal has a convex taper.

19. The connection assembly of claim 14, wherein the shoe of said longitudinal member has a concave taper.

20. The connection assembly of claim 14, wherein the shoe of said longitudinal member has a substantially straight taper.

21. The connection assembly of claim 14, wherein the shoe of said longitudinal member is tapered and the shoe has a lateral edge.

22. The connection assembly of claim 21, wherein the passageway is a slot and at least a portion of the internal wall of the slot is substantially parallel with at least a portion of the lateral edge of the shoe of said longitudinal member.

23. The connection assembly of claim 21, wherein at least a portion of the bore in said housing is complementary tapered to mate with at least a portion of the taper of the shoe of said longitudinal member.

24. The connection assembly of claim 21, wherein the shoe of said longitudinal member has a substantially straight taper.

25. The connection assembly of claim 14, wherein the bore of said longitudinal member opens to the first face and the second face of said housing.

* * * * *

UNITED STATES PATENT AND TRADEMARK OFFICE
CERTIFICATE OF CORRECTION

PATENT NO.   : 6,520,962 B1  Page 1 of 1
DATED        : February 18, 2003
INVENTOR(S)  : Harold S. Taylor and Matthew M. Morrison It is certified that error appears in the above-identified patent and that said Letters Patent is hereby corrected as shown below:

<u>Column 8,</u>
Line 26, please insert the word -- member -- immediately following the word "longitudinal".

Signed and Sealed this

Second Day of September, 2003

JAMES E. ROGAN
*Director of the United States Patent and Trademark Office*